United States Patent [19]

Chaudhari et al.

[11] Patent Number: 4,749,767

[45] Date of Patent: Jun. 7, 1988

[54] STABLE IMIDE-CONTAINING COMPOSITION FROM DIAMINOPHENYLINDANE-BIS-IMIDE, AMINE AND ALKENYL PHENOL OR ETHER

[75] Inventors: Mohammad A. Chaudhari, Bethel; John J. King, Ridgefield, both of Conn.

[73] Assignee: Ciba-Geigy Corporation, Ardsley, N.Y.

[21] Appl. No.: 59,366

[22] Filed: Jun. 8, 1987

Related U.S. Application Data

[62] Division of Ser. No. 809,444, Dec. 16, 1985, Pat. No. 4,689,378.

[51] Int. Cl.$^4$ .............................................. C08G 73/12
[52] U.S. Cl. ................................. 528/170; 428/473.5; 428/500; 528/322

[58] Field of Search ................................ 528/170, 322; 428/473.5, 500

[56] References Cited

U.S. PATENT DOCUMENTS 4,608,426  8/1986  Stern .................................. 528/170
4,689,378  8/1987  Chaudhari et al. ................. 528/322

Primary Examiner—Harold D. Anderson
Attorney, Agent, or Firm—Harry Falber

[57] ABSTRACT

Imide-containing mixture and prepolymer compositions resulting from the combination of diaminophenylindane-bis-maleimide together with amines, alkenyl phenols, alkenyl phenol ethers or mixtures thereof, said compositions being heat curable and suitable for the preparation of prepregs, composites, adhesives, molded articles, coatings, and the like.

18 Claims, No Drawings

STABLE IMIDE-CONTAINING COMPOSITION FROM DIAMINOPHENYLINDANE-BIS-IMIDE, AMINE AND ALKENYL PHENOL OR ETHER

This is a divisional of application Ser. No. 809,444 filed on Dec. 16, 1985 now U.S. Pat. No. 4,689,378.

It is known that polymaleimides can be utilized for the preparation of various polyaddition and polymerization products. Particular emphasis has been placed on bis-maleimide materials which exhibit thermal stability and thus are being more frequently utilized in high performance composite applications.

The currently utilized bis-maleimide systems include aromatic amines or alkenyl phenols as coreactants. U.S. Pat. No. 3,658,764 and U.S. Pat. No. Re. 29,316 are examples of patents that disclose reaction products of unsaturated bis-imides and amines. U.S. Pat. Nos. 4,100,140, 4,127,615, 4,130,600 and 4,131,632 are examples of patents that disclose crosslinked polymers resulting from the reaction of polymaleimides with alkenyl phenols or alkenyl phenol ethers optionally in the presence of epoxy resins. The preferred bis-maleimide in many of these systems is N,N'-4,4'-diphenylmethane-bis-maleimide. It has been noted, however, that such bis-maleimides and the prepolymers thereof are not readily soluble in common organic solvents and, if soluble, are not especially stable in solution form. Such solubility and stability are required in order to provide the desired improved processing conditions and the prolonged storage capability.

It has now been discovered that by utilizing diaminophenylindane-bis-maleimide as the maleimide component, significantly improved products are obtained. Thus, the imide and the resulting mixtures and prepolymers are readily soluble in common organic solvents such as methyl ethyl ketone, acetone, methylene chloride and the like. The resulting materials whether in melt or solution form, are stable at room and elevated temperatures for extended periods of time. The prepolymers exhibit surprisingly high reactivity with the amines and thus can be cured with such amines at comparatively lower temperatures (e.g. 177–200° C.). Upon further heating, the prepolymers convert into high temperature resistant crosslinked polymers with good mechanical, thermal and electrical properties. Curing of the mixtures provides the same. For example, glass transition temperatures of the crosslinked polymers exceed 300° C. The polymers are thus well-suited for use in high performance composites and similar areas of application.

The diaminophenylindane-bis-maleimide corresponds to the formula

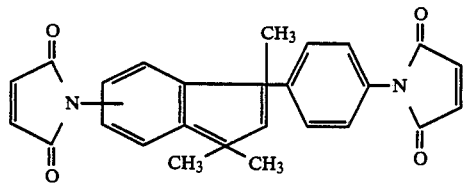

and can be prepared by the reaction of phenylindane diamine and maleic anhydride in the presence of a tertiary amine such as triethylamine and a solvent such as acetone. A further preparative approach may be found in U.S. Pat. No. 4,130,564.

As suitable amines, there may be mentioned aliphatic, cycloaliphatic or aromatic primary and secondary amines, with the aromatic amines particularly $C_6$–$C_{10}$ arylene diamines, being preferred. Typical amines include monoethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3,bis(4-amino-3-methylcyclohexyl)methane, bis(p-aminocyclohexyl)methane, 2,2-bis(4-aminocyclohexyl)propane, 3,5,5-trimethyl-s-(aminomethyl)-cyclohexylamine, N-aminoethyl-piperazine, m-phenylenediamine, p-phenylenediamine, bis(p-aminophenyl)methane, bis(p-aminophenyl)-sulfone, m-xylylenediamine, 1,2-diaminocyclohexane, N,N,N',N'-tetramethyl-4,4'-diamino-diphenylmethane 1,4-diaminocyclohexane, 1,3-bis(aminomethyl)cyclohexane, 1,4-bis(aminomethyl) cyclohexane isophorone diamine, 1-methyl-imidazole and diaminophenylindane. Polyamides are also applicable and are included within the "amine" definition for purposes of this invention.

As the preferred aromatic diamines, there may be mentioned $C_6$–$C_{10}$ arylene diamines such as p-phenylenediamine, m-phenylenediamine and m-xylylenediamine, bis(p-aminophenyl) methane, N,N,N',N'-tetramethyl-4,4'-diaminodiphenylmethane, diaminophenylindane, and the like.

According to the invention, allylphenols and methallylphenols, or the ethers thereof, are preferably employed as the alkenylphenols or alkenylphenol ethers. Both mononuclear and polynuclear, preferably binuclear, alkenylphenols and alkenylphenol ethers can be employed. Preferably, at least one nucleus contains both an alkenyl group and a phenolic, optionally etherified OH group.

As is known, alkenylphenols are manufactured by rearrangement of the alkenyl ethers of phenols (for example of the allyl ether of phenol) by the action of heat (Claisen reaarangement). These alkenyl ethers are also obtained according to known processes by reacting phenols and, for example, allyl chloride in the presence of an alkali metal hydroxide and solvents. As is known, a condensation reaction takes place (elimination of an alkali metal chloride).

Typical examples are:
Compounds of formula I

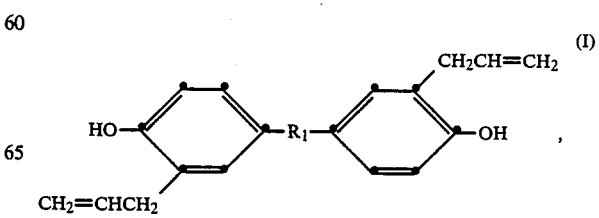

wherein R₁ is a direct bond, methylene, isopropylidene, —O—, —S—, —SO— or —SO₂; Propenyl-substituted phenols of formula II

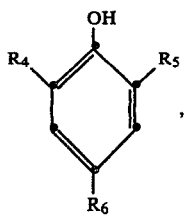

wherein R₄, R₅ and R₆ are each independently a hydrogen atom or C₂-C₁₀ alkenyl, preferably, an allyl or propenyl group, with the proviso that at least one of R₄ to R₆ is alkenyl, preferably a propenyl group;

Compounds of formula III

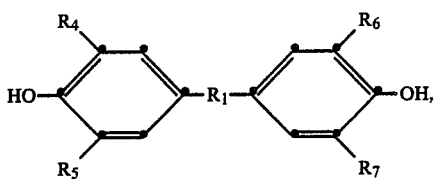

wherein R₄, R₅, R₆ and R₇ are each independently a hydrogen atom or C₂-C₁₀ alkenyl, preferably an allyl or propenyl group, with the proviso that at least one of R₄ to R₇ is alkenyl, preferably a propenyl group, and R₁ is as defined for formula I; and Compounds of formula IV

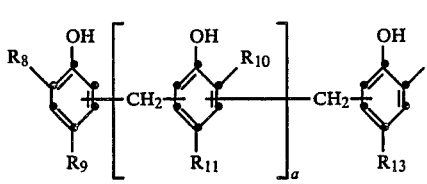

wherein R₈, R₉, R₁₀, R₁₁, R₁₂ and R₁₃ are each independently a hydrogen atom, C₁-C₄alkyl, C₂-C₁₀ alkenyl, preferably allyl or propenyl, with the proviso that at least one of R₈ to R₁₃ is alkenyl, preferably a propenyl group, and a is a value from 0 to 10.

Compounds of formula III are preferred in which each of R₄ and R₆ is a propenyl group and each of R₅ and R₇ is a hydrogen atom and R₁ is methylene, isopropylidene or —O—.

It is also possible to use mixtures of isomers of propenyl- and allyl-substituted mono- or polyhydric phenols. Among the mixtures of isomers it is preferred to use mixtures of propenyl- and allyl-substituted phenols of formula III, preferably those which are obtained by partial isomerization of allyl-substituted phenols of formula IIIa

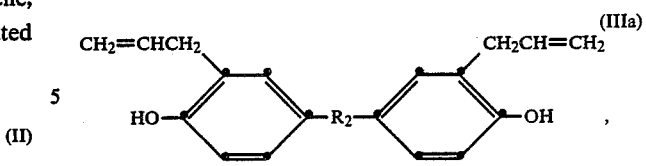

wherein R₂ is methylene, isopropylidene or O.

According to the invention, the use of mixtures of polynuclear alkenylphenols and/or alkenylphenol ethers with mononuclear alkenylphenols and/or alkenylphenol ethers also gives good results. The alkenylphenol ethers preferably employed are those substances which contain one or more molecular radicals of the formula V

in which R₃ denotes an alkyl radical with 1 to 10 C atoms, an aryl radical or an alkenyl radical, preferably allyl or methallyl, the 0 atom in formula V representing the phenolic ether bridge.

A further embodiment of the invention in the use of mixtures of those substances which contain only one OH group and only one alkenyl group on the aromatic nucleus with substances which contain several OH groups and/or several alkenyl groups on the aromatic nucleus, or of mixtures of the corresponding phenol ethers of these substances. The corresponding methallyl compounds can also be used.

Such alkenyl-substituted phenols and polyols are disclosed e.g. in U.S. patent specification Nos. 4,100,140 and 4,371,719.

Typical materials include o,o'-diallyl-bisphenol A, 4,4'-dihydroxy-3,3'-diallyldiphenyl, bis(4-hydroxy-3-allylphenyl)methane, 2,2-bis-(4-hydroxy-3,5-diallylphenyl)propane, eugenol, o,o'-dimethallyl-bisphenol A, 4,4'-dihydroxy-3,3'-dimethallyldiphenyl, bis-(4-hydroxy3-methallylphenyl)methane, 2,2-bis-(4-hydroxy-3,5-dimethallylphenyl)-propane, 4-methallyl-2-methoxyphenol, 2,2-bis-(4-methoxy-3-allylphenyl)propane, 2,2-bis(4-methoxy-3-methallyphenyl)propane, 4,4'-dimethoxy-3,3'-diallyldiphenyl, 4,4'-dimethoxy-3,3'-dimethallyldiphenyl, bis(4-methoxy-3-allylphenyl)methane, bis(4-methoxy-3-methallylphenyl)methane, 2,2-bis-(4-methoxy-3,5-diallylphenyl)propane, 2,2-bis-(4-methoxy-3,5-dimethallylphenyl)propane, 4-allylveratrole and 4-methallyl-veratrole.

In terms of relative concentration, the amine or the alkenyl phenol component or a mixture thereof is employed in a range of 0.05 to 2.0 moles per mole of maleimide, and preferably in a range of 0.1 to 1.0, and most preferably in a 1:1 molar ratio. When mixtures of amines and phenols are present, they are present in relative weight ratios of 19:1 to 1:19 amine to phenol, and preferably 9:1 to 1:9.

The reaction products of this invention may be prepared by merely combining the components to prepare mixtures thereof or to heat the mixture at a temperature of from 75 to 130° C. for a period of about 15 to 60 minutes in order to prepare the prepolymer form. Volatile solvents such as chlorinated hydrocarbons, esters, ether alcohols and tetrahydrofuran may be used to facilitate the reaction. The solvent is then removed to yield the desired prepolymer material.

The subsequent curing of the mixture and prepolymer compositions of this invention is within the knowledge of the art. Curing is effected at temperatures of between 100 to 250° C. for the appropriate period of time.

Upon curing at elevated temperatures, a network of high crosslink density occurs. Accordingly, the expression "cure" as used herein, denotes the conversion of the mixtures or prepolymers into insoluble and infusible crosslinked products, with simultaneous shaping to give shaped articles such as castings, pressings or laminates, or to give two dimensional structures such as coatings, enamels or adhesive bonds. The modified systems are advantageous for the formation of coatings because of the improved toughness of the resulting cured coatings.

The mixtures and prepolymers prepared according to the invention can furthermore be mixed, at any stage before cure, with usual modifiers such as extenders, fillers and reinforcing agents, pigments, dyestuffs, organic solvents, plasticizers, tackifiers, rubbers, accelerators, diluents, and the like. As extenders, reinforcing agents, fillers and pigments which can be employed in the curable mixtures according to the invention there may be mentioned, for example: coal tar, bitumen, glass fibers, boron fibers, carbon fibers, cellulose, polyethylene powder, polypropylene powder, mica, asbestos, quartz powder, gypsum, antimony trioxide, bentones, silica aerogel ("aerosil"), lithopone, barite, titanium dioxide, carbon black, graphite, iron oxide, or metal powders such as aluminum powder or iron powder. It is also possible to add other usual additives, for example, flameproofing agents, agents for conferring thixotropy, flow control agents such as silicones, cellulose acetate butyrate, polyvinyl butyrate, waxes, stearates and the like (which are in part also used as mold release agents) to the curable mixtures.

It is also possible in adhesive formulations, for example, to add rubbers such as carboxyl-terminated acrylonitrile-butadiene rubber, modifying resins such as triglycidyl p-aminophenol and accelerators such as boron trifluoride monoethylamine complexes or imidazole complexes.

The curable mixtures can be manufactured in the usual manner with the aid of known mixing equipment (stirrers, kneaders, rollers and the like).

The mixtures and prepolymers of this invention are distinguished by high reactivity, ready solubility in common solvents, stability in melt or solution form and good thermal mechanical properties of the products when properly cured, for example, good flexural and shear strength or interlaminar shear strength. Products obtained with them have good mechanical, thermal and electrical properties, have high glass transition temperatures and are substantially non-brittle. The mixtures and prepolymers of this invention can also be readily applied from the melt, especially without the addition of non-volatile solvents, for example, for impregnation.

Mixtures and prepolymers such as those described above have application in a broad range of end uses such as in composites, printed circuit boards, castings, molding compounds, adhesives and coatings. In view of the improved performance characteristics, the application of greatest interest is in high performance composite applications, pertinent, for example, to the aerospace industry. Thus, the modified resins are utilized to pre-impregnate various fibers for eventual use as honeycomb skins or structural parts. Techniques for preparing prepregs are well known to those skilled in the art. In terms of honeycomb skins and structural parts, graphite, glass, Kevlar reinforced skins and parts as well as others, can be readily prepared from the instant systems. Correspondingly, techniques for preparing laminates are well known. Such laminates may be prepared by compression or autoclave molding and may comprise a broad range of thicknesses. A further preferred area of use is adhesion promotion wherein the instant systems effectively improve adhesive performance characteristics.

The following examples illustrate the preferred embodiments of this invention. In these examples, all parts given are by weight unless otherwise noted.

EXAMPLE 1

A prepolymer is prepared by reacting 438 grams (1 mole) of diaminophenylindane-bis-maleimide and 308 grams (1 mole) of o,o'-diallyl-bisphenol A at a temperature of 100–120° C. for 30–60 minutes with constant stirring and under vacuum conditions. The resulting prepolymer is a clear, viscous liquid.

The prepolymer is then dissolved at 50%, by weight, solids in methyl ethyl ketone. Complete dissolution with no appearance change is noted. The solution is then maintained at room temperature for a period of >26 weeks. No settling of solids or change in viscosity is noted.

EXAMPLE 2

Cured resin plaques are prepared utilizing the prepolymer of Example 1 after degassing at 26 +inches Hg of vacuum for 15 minutes. The molten solution is then poured into ⅛" thick sheet molds and cured by the following cure cycle:
1 hr. @180° C.
2 hrs. @200° C.
6 hrs. @250° C.
A fully cured panel is thus obtained.

EXAMPLE 3

The glass transition temperature of the crosslinked resin of Example 2 is determined on a Perkin-Elmer TMA run at 20° C./min. in the penetration mode with a 40 g. weight. Tg is 297° C.

The system is likewise tested for room temperature tensile properties (ASTM D-638) and flexural properties (ASTM D-790) with the following results.

| | |
|---|---|
| Tensile strength (ksi) | 9.0 |
| Tensile Modulus (ksi) | 574 |
| Tensile elongation (%) | 1.8 |
| Flex strength (ksi) | 17.4 |

| | |
|---|---|
| Flex modulus (ksi) | 561 |

These data thus substantiate the improved characteristics of the composition of this invention.

EXAMPLE 4

The procedure of Example 1 is repeated with the exception that 37.8 grams of bis(p-aminophenyl)methane is added thereto. The resulting prepolymer is a clear, viscous liquid at 75–130° C.

EXAMPLE 5

The procedure of Example 4 is repeated with the exception that diaminophenylindane is used in place of the bis(p-aminophenyl)methane. The resulting prepolymer is a clear, viscous liquid at 75–130° C.

EXAMPLE 6

The gel time indicative of degree of reactivity is determined on the systems of this invention as well as on a 1:1 molar combination of 4,4'-bismaleimidodiphenyl-methane and o,o'-diallyl bisphenol A (Ex. A). Thus, each system is placed in an open container and heated on a hot plate at 177° C. The time to observation at gel formation is noted. Faster times are indicative of the potential for reduced processing, the lack of need for curing catalysts and the reduced likelihood of bleeding and other adverse characteristics.

| | Gel Time (minutes) |
|---|---|
| Ex. 1 | 14.5 |
| Ex. 4 | 3.0 |
| Ex. 5 | 4.0 |
| Ex. A | 20.0 |

EXAMPLE 7

Differential scanning calorimetry utilizing a DuPont calorimeter is conducted on a number of samples to obtain an indication of reactivity and melt stability. The testing is conducted under a nitrogen atmosphere at a temperature increase rate of 10° /minute. The samples utilized are:

Ex. B—Adduct of 4,4'-bismaleimidodiphenylmethane and bis(p-aminophenyl)methane (KERIMID 601) plus stoichiometric amount of bis(p-aminophenyl)methane curing agent Ex. C—Blend of bismaleimides (KERIMID 353) plus stoichiometric amount of bis(p-aminophenyl)methane curing agent Ex. 7—Prepolymer of 1:1 molar ratio of diaminophenylindane-bis-maleimide and bis(p-aminophenyl)methane The following results are obtained:

| Ex. | Maximum Peak Temp. (°C.) |
|---|---|
| B | 206 |
| C | 193 |
| 7 | 115 |

The lower temperature for the system of this invention is indicative of desired quicker curing, easier processing and greater stability.

Furthermore, a review of the endotherm-exotherm curves for the respective systems reveals that the system of this invention (Ex. 7) exhibits a rapid, steep incline from the point of maximum endotherm to the point of maximum exotherm. This pattern is indicative of excellent melt stability since the melt form is short lived and thus not available to the degradative effects. In contrast, the prior materials B and C exhibit plateaus between the endotherm and exotherm making them more available to degradative effects.

Summarizing, it is seen that this invention provides improved maleimide systems, said improvements stemming from the introduction of diaminophenylindane-bis-maleimide. Variations may be made in procedures, proportions and materials without departing from the scope of the invention as defined by the following claims.

What is claimed is:

1. A heat curable composition comprising the mixture or prepolymer reaction product of (a) diaminophenylindane-bis-maleimide, and (b) an amine, or a mixture of an amine and an alkenyl phenol or an alkenyl phenol ether.

2. The composition of claim 1 as a mixture.

3. The composition of claim 1 as a prepolymer reaction product.

4. The composition of claim 1, wherein component (b) is present in a concentration of from 0.05 to 2.0 moles per mole of component (a).

5. The composition of claim 4, wherein components (a) and (b) are present in equimolar amounts.

6. The composition of claim 1, wherein said amine in component (b) is an aromatic diamine selected from the group consisting of $C_6$–$C_{10}$ arylene diamines, bis(p-aminophenyl)methane, N,N,N',N',tetramethyl-4,4'-diaminodiphenylmethane and diaminophenylindane.

7. The composition of claim 6, wherein said aromatic diamine is bi(p-aminophenyl)methane or diaminophenylindane.

8. The composition of claim 11, wherein said phenol in component (b) is an alkenyl phenol corresponding to the formulae

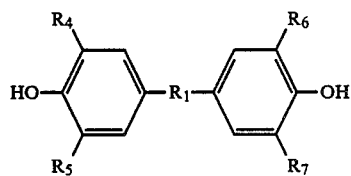

wherein $R_1$ is a direct bond, or $R_1$ is methylene, isopropylidene, —O—, —S—, —SO— or —$SO_2$—; and $R_4$, $R_5$, $R_6$ and $R_7$ are independently hydrogen or $C_2$–$C_{10}$ alkenyl, with the proviso that at least one of $R_4$–$R_7$ is an alkenyl group;

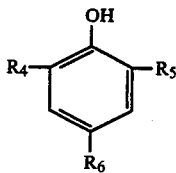

wherein $R_4$, $R_5$ and $R_6$ are independently hydrogen or $C_2-C_{10}$ alkenyl, with the proviso that at least one of $R_4-R_6$ is alkenyl; and

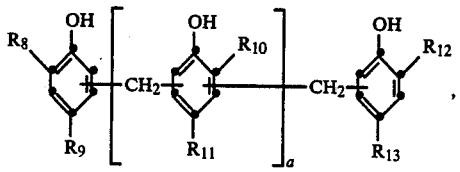

wherein $R_8$, $R_9$, $R_{10}$, $R_{11}$, $R_{12}$ and $R_{13}$ are independently hydrogen, $C_1-C_4$ alkyl or $C_2-C_{10}$ alkenyl, with the proviso that at least one of $R_8-R_{13}$ is alkenyl; or the ethers thereof containing at least one —$OR_3$ radical wherein $R_3$ is $C_1-C_{10}$ alkyl, aryl or alkenyl.

9. The composition of claim 8, wherein said alkenyl group is allyl or propenyl.

10. The composition of claim 9, wherein said alkenyl phenol is o,o'-diallyl-bisphenol A.

11. The composition of claim 1, wherein component (b) is a mixture of amine and phenol in a 19:1 to 1:19 weight ratio.

12. The composition of claim 11, wherein said weight ratio is 9:1 to 1:9.

13. The composition of claim 11, wherein component (b) is a mixture of o,o'-diallyl-bisphenol A and bis(p-aminophenyl)methane.

14. The composition of claim 11, wherein component (b) is a mixture of o,o'-diallyl-bisphenol A and diaminophenylindane.

15. The product obtained by curing the mixture of claim 2.

16. The product obtained by curing the prepolymer reaction product of claim 3.

17. A laminate structure comprising the cured product of a wound yarn impregnated with the mixture of claim 2.

18. A laminate structure comprising the cured product of a wound yarn impregnated with the prepolymer reaction product of claim 3.

* * * * *